(12) United States Patent
Rajagopalan et al.

(10) Patent No.: US 11,286,179 B2
(45) Date of Patent: Mar. 29, 2022

(54) FLOW-THROUGH FLUID PURIFICATION DEVICE AND MEANS FOR ACCOMMODATING A RADIATION SOURCE

(71) Applicant: Merck Patent GmbH, Darmstadt (DE)

(72) Inventors: Pascal Rajagopalan, Palaiseau (FR); Julien Gross, Elancourt (FR); Ichiro Kano, Montigny le Bretonneux (FR)

(73) Assignee: Merck Patent GmbH

( * ) Notice: Subject to any disclaimer, the term of this patent is extended or adjusted under 35 U.S.C. 154(b) by 0 days.

(21) Appl. No.: 16/485,830

(22) PCT Filed: Feb. 20, 2018

(86) PCT No.: PCT/EP2018/054073
§ 371 (c)(1),
(2) Date: Aug. 14, 2019

(87) PCT Pub. No.: WO2018/153827
PCT Pub. Date: Aug. 30, 2018

(65) Prior Publication Data
US 2020/0062615 A1 Feb. 27, 2020

(30) Foreign Application Priority Data
Feb. 23, 2017 (EP) .................... 17290025

(51) Int. Cl.
*A61L 2/10* (2006.01)
*C02F 1/32* (2006.01)
*C02F 103/04* (2006.01)

(52) U.S. Cl.
CPC ............ *C02F 1/325* (2013.01); *A61L 2/10* (2013.01); *C02F 2103/04* (2013.01); *C02F 2201/328* (2013.01); *C02F 2201/3223* (2013.01)

(58) Field of Classification Search
CPC ...................................................... G02F 1/325
(Continued)

(56) References Cited

U.S. PATENT DOCUMENTS

| | | | |
|---|---|---|---|
| 5,352,359 A | * | 10/1994 | Nagai .................. C02F 1/325 210/192 |
| 5,372,781 A | | 12/1994 | Hallett et al. |

(Continued)

FOREIGN PATENT DOCUMENTS

| | | |
|---|---|---|
| CH | 683517 A5 | 3/1994 |
| CN | 1655828 A | 8/2005 |

(Continued)

OTHER PUBLICATIONS

Dallan, "Ultraviolet Light in TOC Reduction", Water Conditioning & Purification, pp. 36-37, Jun. 2002.

(Continued)

*Primary Examiner* — Phillip A Johnston
(74) *Attorney, Agent, or Firm* — Nields, Lemack & Frame, LLC

(57) ABSTRACT

A flow-through fluid purification device (1), which comprises a container (5) arranged such that fluid to be purified can flow-through a volume (8) of the container (5) from an inlet (3) to an outlet (7), a receptacle (10) for accommodating a radiation source in the form of a lamp (13), wherein the receptacle (10) has an interface wall (11) permeable for radiation with a wavelength in the UV-range, preferably between 150 nm and 200 nm, more preferably of 172±8 nm, and arranged to let radiation pass into the volume (8) of the container (5), a plurality of baffle plates (9) located in the volume (8) of the container (5) with an inter-baffle distance (D) in the flow direction from the inlet (3) to the outlet (7), wherein the baffle plates (9) are arranged to force the fluid flowing from the inlet (3) to the outlet (7) to flow substan- (Continued)

tially along the interface wall (11) and through gaps (G) between the interface wall (11) and the baffle plates (9) defining the shortest distance between the interface wall (11) and the baffle plates (9), and wherein the baffle plates (9) each have a surface on the upstream side in the flow direction which is perpendicular to the interface wall (11).

17 Claims, 9 Drawing Sheets

(58) Field of Classification Search
USPC .................................................. 250/504 R
See application file for complete search history.

(56) References Cited

U.S. PATENT DOCUMENTS

| | | | |
|---|---|---|---|
| 8,541,758 B1* | 9/2013 | Filson, II | C02F 1/325 250/455.11 |
| 8,591,730 B2* | 11/2013 | Yong | B01J 19/006 210/153 |
| 2007/0003430 A1 | 1/2007 | Kaiser et al. | |
| 2010/0078574 A1* | 4/2010 | Cooper | A61L 2/0047 250/455.11 |
| 2011/0024365 A1 | 2/2011 | Yong et al. | |
| 2011/0318237 A1 | 12/2011 | Woodling et al. | |
| 2014/0263090 A1 | 9/2014 | Yencho | |
| 2020/0048111 A1 | 2/2020 | Roitel et al. | |

FOREIGN PATENT DOCUMENTS

| | | |
|---|---|---|
| CN | 101112680 A | 1/2008 |
| CN | 102482121 A | 5/2012 |
| CN | 103864172 A | 6/2014 |
| DE | 102010014712 B3 | 6/2011 |
| EP | 2309258 A1 | 4/2011 |
| JP | 1-174093 U | 12/1989 |
| JP | 3-61982 U | 6/1991 |
| JP | 10-43753 A | 2/1998 |
| JP | 2000-61459 A | 2/2000 |
| JP | 2013-166126 A | 8/2013 |
| JP | 2017-176994 A | 10/2017 |
| WO | WO 9515294 * | 10/1994 ............ C02F 1/325 |
| WO | 95/15294 A1 | 6/1995 |
| WO | 2006/100876 A1 | 9/2006 |
| WO | 2010/117809 A2 | 10/2010 |
| WO | 2010/125389 A1 | 11/2010 |
| WO | 2011/014717 A2 | 2/2011 |
| WO | 2011/162877 A1 | 12/2011 |
| WO | 2014/148325 A1 | 9/2014 |

OTHER PUBLICATIONS

Oppenlander et al., "Improved vacuum-UV (VUV)-initiated photomineralization of organic compounds in water with a xenon excimer flow-through photoreactor (Xe2 lamp, 172 nm) containing an axially centered ceramic oxygenator", Chemosphere, vol. 60, pp. 302-309, 2005.
Sosnin et al., "Applications of capacitive and barrier discharge excilamps in photoscience", Journal of Photochemistry and Photobiology C: Photochemistry Reviews, vol. 7, pp. 145-163, 2006.
Chinese communication, with English translation, dated Aug. 26, 2021 in co-pending Chinese patent application No. 201880013547.1.
International Search Report and Written Opinion dated Apr. 12, 2018 in corresponding PCT application No. PCT/EP2018/054073.
International Search Report and Written Opinion dated May 2, 2018 in co-pending PCT application No. PCT/EP2018/054061.
Japanese communication, with English translation, dated Jan. 6, 2022 in corresponding Japanese patent application No. 2019-545965.
Japanese communication, with English translation, dated Jan. 5, 2022 in co-pending Japanese patent application No. 2019-545917.

* cited by examiner

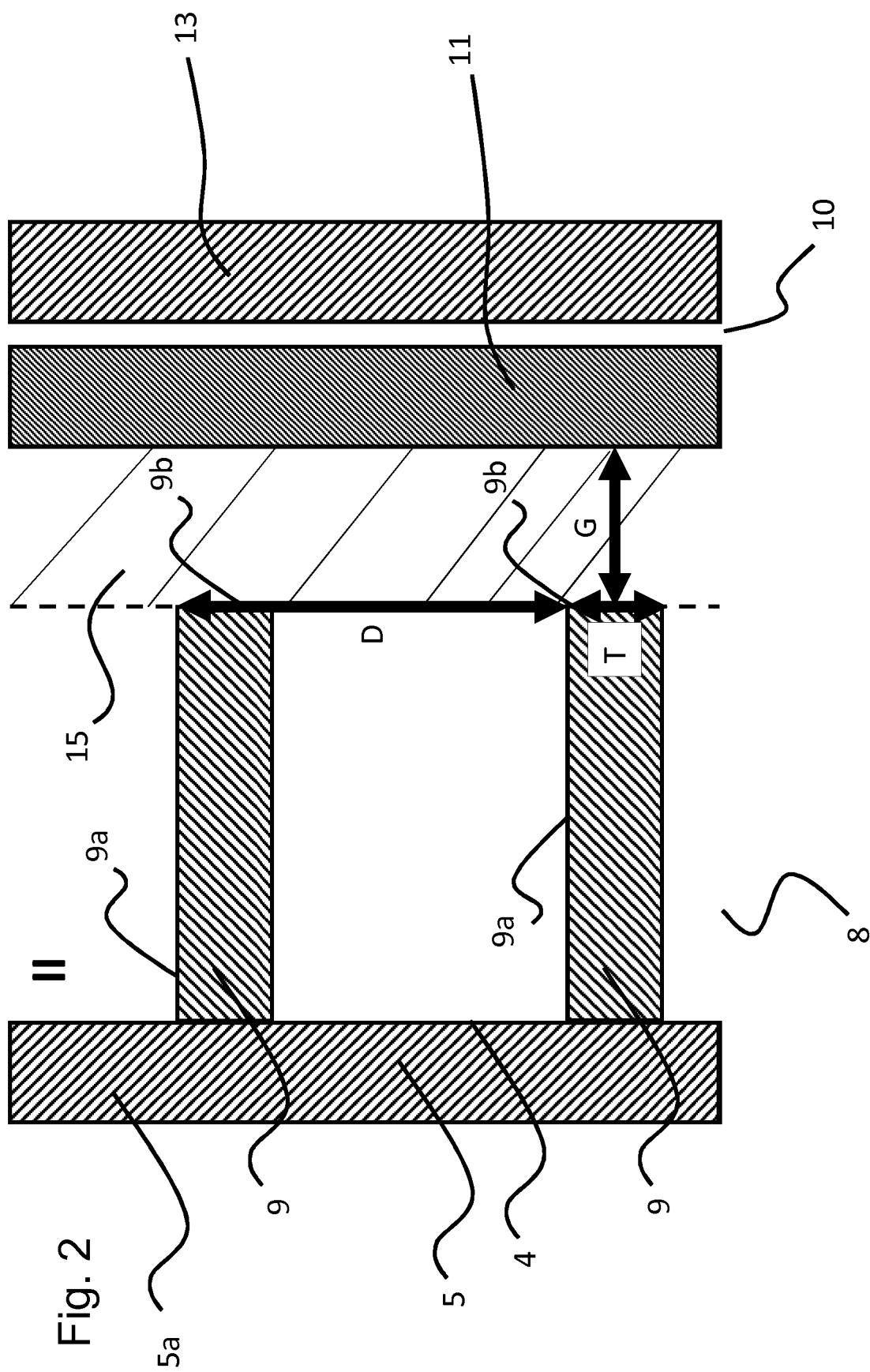

FLOW-THROUGH FLUID PURIFICATION DEVICE AND MEANS FOR ACCOMMODATING A RADIATION SOURCE

The invention relates to a flow-through fluid purification device for purifying a fluid, preferably by oxidizing organics contained in pure or ultra-pure water. The invention also preferably relates to such flow-through fluid purification devices that are designed for laboratory scale water purification applications with a maximum throughput volume of 2 l/min.

BACKGROUND

Devices are known which provide the possibility to purify a fluid, preferably to produce pure or ultra-pure water, by oxidizing organics contained in the fluid in that the fluid is exposed to UV-C radiation while it flows through a container of the device.

Ultrapure water can be defined as the highest quality reagent grade water that exceeds ASTM D5127 standards and that has a total organic carbon (TOC) of less than 5 parts per billion (ppb).

UV radiation according to DIN 5031 part 7 is defined as radiation having a wavelength in a range between 100 nm and 380 nm. A sub range of this range including wavelengths shorter than 280 nm is the UV-C range and a further sub range including wavelengths shorter than 200 nm is the vacuum UV-C range (VUV).

The purification, to which the present invention pertains, aims at reducing the TOC content in the fluid flowing through the device through organic oxidizing reactions induced by the UV-C radiation.

Common flow-through purification devices which are based on oxidation by UV radiation are using, as a radiation source, a mercury gas lamp. The lamp is arranged such that it irradiates the fluid flowing through a container. In the oxidation reaction induced by the UV-irradiation the organics contained in the fluid are degraded into carbonates and byproducts comprising intermediate ions other than carbonates and which can be filtered out of the fluid after purification. The oxidizing reaction includes an intermediate step of decomposing water molecules into different reactive intermediates including radical, neutral and ionic intermediates. The radical intermediates subsequently oxidize organics contained in the fluid into carbon dioxide and water. UV-light with a wavelength of 185 nm is known to effectively generate such radical intermediates.

It is also known to use excimer lamps for germicidal water purification. Such lamps are based on the excitation of, for example, a xenon gas to an excimer state. The wavelength of the radiation emitted during excitation and de-excitation is 172 nm or below (depending on the gas used in the lamp). This wavelength is too low to be directly used for water purification applications and it has a very low water transparency.

WO 2014/148325A1 discloses to use such excimer lamp in combination with a translucent coating on the lamp to shift the emitted wavelength to higher wavelengths. The additional coating adds, however, to the cost, has a reduced lifetime due to a degradation of the coating with time due to UV-exposure, and has a reduced performance because the coating absorbs around 50% of the radiation and restitutes only 50% of the absorbed energy.

WO 95/15294A1 discloses a sterilizer for water and other fluids that utilize ionizing UV-radiation as a sterilizing means. A cylindrical UV lamp as a radiation source is centrally housed in a tubular air chamber which in return is positioned coaxially within the interior of a housing forming an elongate exposure chamber through which the fluid flows from an inlet at one axial end portion to an outlet at an opposite axial end portion. An array of baffles in the form of coaxially disposed toroidal disks spans the interior of the exposure chamber with each baffle partly blocking the passage of fluid as it flows through the chamber along the axial extension. Each baffle is provided with a channel between the edge of the baffle and the inner peripheral wall of the chamber to permit fluid to flow past the baffle at a portion adjacent to the chamber wall and the channels of neighboring baffles are offset from each other to generate a sinuous and turbulent flow of the fluid as it traverses the length of the chamber. Thus, the fluid stream is sequentially diverted towards and away from the radiation source. An air channel may be channeled through the air chamber for the co-production of ozone and the ozone may in turn be reacted with the water either prior or subsequent to the treatment of the water with the UV radiation. In this flow-through device significant portions of the fluid to be purified can pass through the device with relative large distances from the radiation source, thereby potentially suffering from incomplete purification.

The document US 200710003430A1 discloses a method of inactivating microorganisms such as viruses within a fluid. The inactivating process is based on the use of an elongated UV lamp emitting radiation between 180 and 320 nm, preferably between 225 and 290 nm, surrounded by an elongated reaction chamber through which a primary flow directed along the length of the UV lamp is generated from an inlet to an outlet. A circulating secondary flow is superimposed on the primary flow and both, the primary and secondary flow, are generated by a rotating agitator disposed within the reaction chamber or by a spiral wound tube surrounding the UV lamp and defining a helical channel that spirals around the UV lamp and approaches but does not engage the UV lamp and has a D-shaped cross section. This flow-through purification is relatively complex and has high manufacturing costs.

The prior art purification devices using UV radiation frequently employ mercury based UV lamps to produce the desired wavelength radiation. Mercury based UV lamps, are, however, generally problematic as they require extreme care in handling and special treatment or disposal procedures due to the hazardous nature of the mercury.

OBJECT OF THE INVENTION

An object to be solved is to provide a flow-through fluid purification device for purifying a fluid, preferably for producing pure or ultra-pure water, which avoids the use of mercury lamps, has a high purification efficiency and is cost effective.

SOLUTION OF THE PROBLEM

According to the present invention this object is accomplished by a flow-through fluid purification device with the features of claim 1. Preferred embodiments are defined in the dependent claims.

The flow-through fluid purification device of the present invention comprises a container arranged such that fluid to be purified can flow-through volume of the container from an inlet to an outlet; a receptacle for accommodating a radiation source in the form of a lamp, whereby the receptacle has an interface wall permeable for radiation with a wavelength in the UV-range, preferably between 150 nm and 200 nm, more preferably of 172±8 nm, and arranged to let radiation pass into the volume of the container; a plurality of baffle plates located in the volume of the container with an inter-baffle distance in the flow direction from the inlet to the outlet, wherein the baffle plates are arranged to force the fluid flowing from the inlet to the outlet to flow substantially along the interface wall and through gaps between the interface wall and the baffle plates defining the shortest distance between the interface wall and the baffle plates; and wherein the baffle plates each have at least one surface on the upstream side in the flow direction, which is perpendicular to the flow direction.

The baffle plates in the device according to invention and the narrow gaps between the baffle plates and the interface wall to the radiation source generate a small fluid wall thickness along the interface wall so that substantially all the fluid is exposed to the radiation even if a mercury free radiation source like an excimer lamp with a relatively low wavelength in the range of 150 nm to 200 nm is used that has a relatively low transmission through water. Further, the baffles generate just sufficient turbulences in the fluid in the immediate vicinity of the interface wall to the radiation source, especially through having at least one surface perpendicular to the flow direction of the fluid, that the fluid flow is not laminar but is intermixed without reducing the flow rate along the length of the device. The intermixing secures uniform exposure times of the fluid to the radiation and produces a uniform purity level, i.e. a low TOC, of the fluid that has passed the device and a higher TOC reduction can be achieved for a given flow rate and a given lamp size.

Further, in an existing device, a lower intensity lamp can be used or lamp ageing is affecting the performance to a smaller extent. Also, the capacity to ionize more complex organics is improved.

Since substantially all the fluid is forced to flow in the narrow zone along the interface wall by the gaps between the interface wall and the baffle plates which function as constrictions and narrow the fluid flow, a complete penetration of the radiation through the fluid flow is achieved.

According to a preferred embodiment the gaps between the interface wall and the baffle plates, i.e. the shortest distances, are equal to or smaller than 2.0 mm, preferably in the range from 1.2 mm to 0.3 mm, more preferably in the range from 0.5 mm to 1.0 mm. Preferably, the baffle plates have a thickness parallel to the interface wall, at least in a portion adjacent to the gap, of less than 1.5 mm, preferably of less than 1.0 mm.

The smaller, i.e. thinner the active oxidation layer is, the more efficiently the TOC concentration can be decreased. Moreover, a smaller gap size leads to a better production of turbulences. On the other hand, the overall flow rate of the fluid through the device and thus the pressure drop is reduced with smaller gap sizes and longer gap lengths defined by the thickness of the baffle plates. The preferred gap sizes and dimensions provide an optimal balance between the flow rate of the fluid and the level of purity in the fluid and thus increase the overall efficiency of the device.

According to another preferred embodiment the inter-baffle distance in the flow direction between the upstream surfaces of two consecutive baffle plates, at least adjacent to the gap, is in the range from 4 and 30 mm, preferably between 10 and 20 mm, more preferably around 10 mm. Preferably, the number of baffle plates in the flow direction along the interface wall is at least 4, preferably 8 to 12.

The inter-baffle distance and the number of baffles in these ranges have been determined to provide the best performance and purification efficiency at a flowrate of 120 liters per hour (l/h) through the device. For higher flow rates a scale up of the device can be performed.

According to another preferred embodiment the baffle plates are arranged in a stack and are interconnected with each other, preferably through spacers defining the inter-baffle distance, to form a self-supporting element that can be pre-fabricated separately from the container and easily mounted into the volume of the container. Preferably, a seal is provided between the inner peripheral wall of the container and the baffle plates and the seal can be provided as a separate component or material or can be formed by the material of the baffles if it has a certain elasticity and the outer dimensions are slightly larger than the inner dimensions of the container.

The self-supporting structure of the baffles plates provides advantages with respect to manufacturing and maintenance ease and cost. Further, a range of devices with different size, capacity and throughput can be easily set up with a small number of different components in a modular construction.

According to another preferred embodiment the baffle plates are formed as disks interconnected with spacers, wherein the baffles may be formed from metal, preferably stainless steel.

This embodiment provides the possibility of easily changing the inter-baffle distance by using different spacers and of simply manufacturing the baffles, i.e. by stamping them out from a sheet material like metal. In particular, stainless steel is a preferred material for the use in the pharmaceutical industry, the food industry and the like and in the context of the present invention metal (especially stainless steel) has a good UV stability with respect to the wavelengths of the radiation source and is inert to not interact with the fluid.

According to another preferred embodiment the baffle plates are integrally formed with the inner peripheral wall of the container. Preferably, the baffle plates are formed from plastics materials that have UV stability, preferably from fluoropolymer materials, especially polytetrafluorethylen (PTFE), PVDF, PEEK, PFA, or polyetherimide (PEI), or PE, preferably provided with a metallic coating.

Using plastics materials as the material for the baffle plates makes it unnecessary to meet strict manufacturing tolerances, compared with metal or the like, due to the elasticity of material that can, in a certain range, overcome small manufacturing faults. As a side effect a seal between the baffle plates and the container wall can be automatically provided by the flexibility of the plastics material in conjunction with an appropriate dimensioning of the baffle plates in relation to the dimensions of the container.

Preferably, UV stability can be reached through UV stabilizers, such as benzophenones, contained in the plastics material and can prevent the formation of free radicals and extend the service life of the device.

Furthermore, the metallic coating provides the above mentioned advantageous of using a metal as raw material for the baffle plates, but this effect can be reached at lower costs due to the more effective use of the comparatively expensive raw material metal.

According to another preferred embodiment the container has an outer cylinder, the interface wall of the receptacle is formed by an outer peripheral wall of an inner cylinder inserted into the volume of the outer cylinder with the baffle plates located between the outer cylinder and the inner cylinder, and the device has at least one end cap engaged with an axial end of the outer cylinder, arranged to hold the inner cylinder in position in the outer cylinder and to fluid-tightly close the outer cylinder. The outer and inner cylinders and the baffle plates are preferably concentric.

According to another preferred embodiment the interface wall comprises or is substantially completely formed from quartz glass.

According to another preferred embodiment the radiation source is an excimer lamp configured to emit radiation with a wavelength in the UV-range, preferable between 150 nm and 200 nm, more preferably of 172±8 nm, wherein the radiation source is located so as to be separated from the fluid in the volume of the container by the interface wall.

BRIEF DESCRIPTION OF DRAWINGS

FIG. 2 is an enlarged view of an area II of FIG. 1;

DETAILED DESCRIPTION OF PREFERRED EMBODIMENTS

Hereinafter, embodiments of the present invention will be described with reference to the accompanying drawings.

The device according to the invention is specifically suitable for reducing the TOC content of water to produce pure or ultrapure water utilizing an oxidization reaction but the invention is not limited to this field of application but can be generally applied to flow-through devices exposing a stream of fluid to a radiation source.

An oxidization reaction induced by radiation, which is also known as a photo-oxidation reaction, can take place in a fluid containing organic carbon when it is exposed to radiation, in the present context to radiation with a wavelength below 200 nm that can be produced using excimer lamps as the radiation source that are free of mercury. Upon exposure to the radiation the organic carbon compounds contained within the fluid oxidize and carbonates and byproducts comprising intermediate ions other than carbonates are formed.

Figure 1:
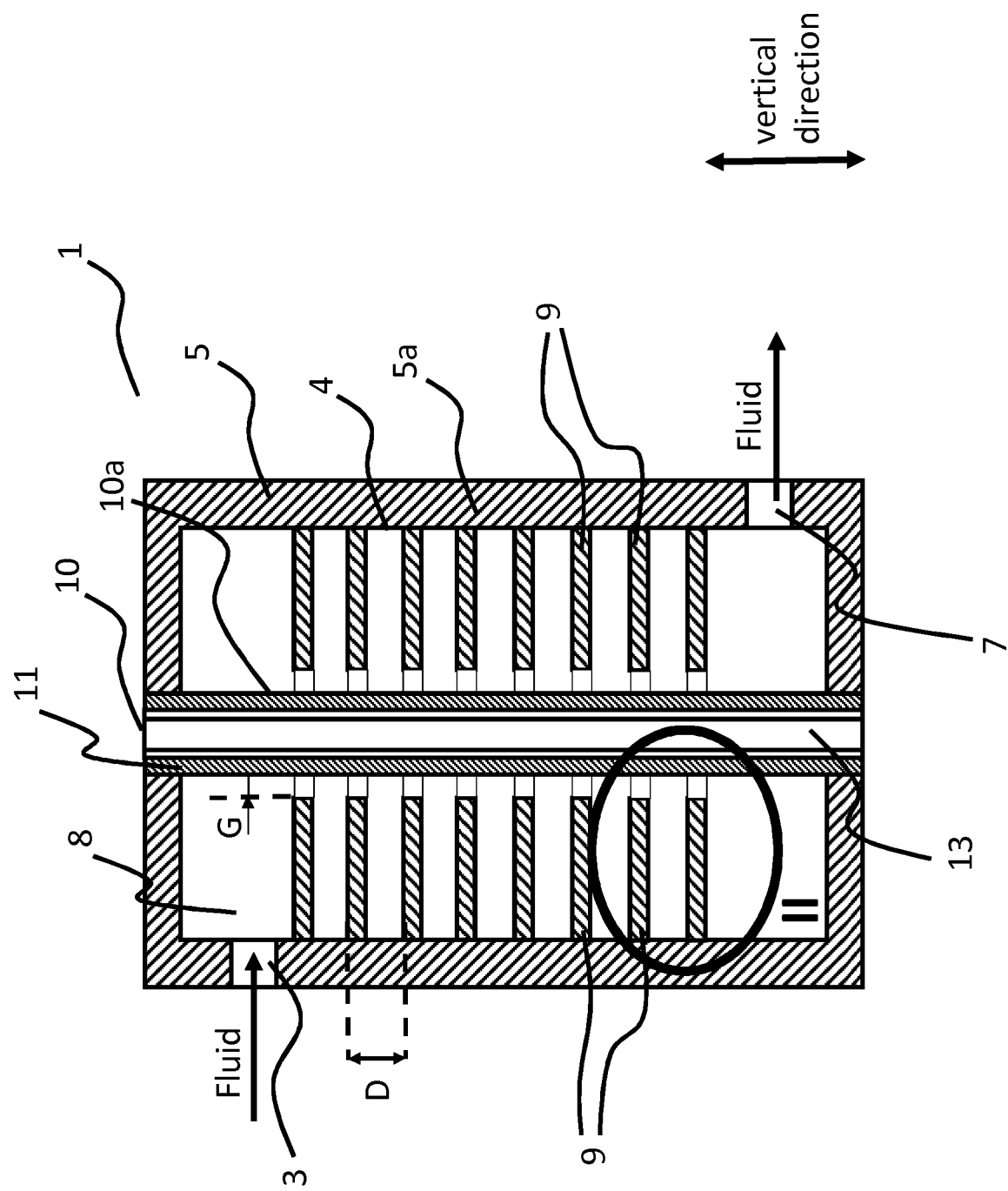
FIG. 1 shows a schematic section view of a purification device according to an embodiment of the present invention.

As schematically shown in FIG. 1, the purification device 1 generally has an axially elongated cylindrical container 5 with an outer cylinder 5a which has an inlet 3 for a fluid to be purified located at an axial end portion of the container 5 (on a vertical upper side of the outer container 5a in the posture of FIG. 1), and an outlet 7 for a purified fluid located at an opposite axial end portion of the container 5 (on a vertical lower side of the outer cylinder 5a in the posture of FIG. 1). An exposure zone for the fluid to be purified is located between the inlet 3 and outlet 7 and defines an active reactor length. The specific structure and location of the inlet 3 and outlet 7 is not particularly relevant as long as a continuous flow through the exposure zone of the device 1 can be created.

In order to make use of the gravitation to force the fluid to flow through the exposure zone the device 1 can be arranged such that the inlet 3 is at the vertical upper side and the outlet 7 is located at the vertical lower side as shown in FIG. 1. More preferably, the device 1 is operated upside down by employing a pump (not shown) to force the fluid from an inlet 3 at the vertical lower side of the device 1 up to an outlet 7 at the vertical upper side in order to efficiently suppress building of air bubbles in the fluid. The vertical posture is preferred as it equalizes the distribution about the circumference where the baffle plates to be described later are substantially perpendicular to the longitudinal direction of the container 5.

In this schematic embodiment eight baffle plates 9 are arranged in the exposure zone inside the container 5 outer cylinder 5a. Each baffle plate 9 has two horizontal surfaces which are substantially perpendicular to the longitudinal axis of the outer cylinder 5a which corresponds to the flow direction of the fluid through the container 5. The baffle plates 9 also have a vertical surface parallel to the fluid flow direction and facing a wall (interface wall 11) of an inner container or receptacle to be described later. The invention is not limited to eight baffle plates 9 and may include for example four, preferably eight to twelve baffle plates. The optimum number of baffle plates 9 can be determined in relation to the container length and diameter, i.e. the desired flow volume. For example, in a device with an exposure zone (active reactor length) of approximately 10 cm and an inner diameter of the outer cylinder of approximately 25 mm 10 baffle plates have been determined to provide optimum performance.

The baffle plates 9 have a thickness T of less than 1.5 mm, preferably less than 1.0 mm and may be formed from sheet or plate material of metal, preferably stainless steel, or from plastics materials that have UV stability, preferably from fluoropolymer materials, especially polytetrafluoroethylene (PTFE), PVDF, PEEK, PFA, or polyetherimide (PEI), or PE, preferably provided with a metallic coating.

The baffle plates 9 are, in this embodiment, integrally formed with a surface of an inner peripheral wall 4 of the outer cylinder 5a and have a centric hole with an inner diameter that is larger than an outer diameter of the inner cylinder 10a inserted into the outer cylinder 5a and sealed in the container such that no fluid can enter the interior space of the inner cylinder 10a. The inner cylinder 10a thus forms the interface wall 11 to the exposure zone in the volume 8 of the outer cylinder 5.

The inner cylinder 10a is located concentric inside the outer cylinder 5 and forms a receptacle 10a to accommodate a radiation source (excimer lamp) 13 inside and separate it from the exposure zone in the volume 8 of the container 5 where the fluid to be purified flows. The interface wall 11 of the inner cylinder 10a is therefore permeable at least for radiation with a wavelength in the UV-range, preferable at least between 150 nm and 200 nm, more preferably of 172±8 nm.

The baffle plates 9 are arranged with a predetermined distance (inter-baffle distance) D in the axial direction of the container 5 between the upstream horizontal surfaces of respective adjacent baffle plates. The inter-baffle distance D in the flow direction between the upstream surfaces along the interface wall 11 is between 4 and 30 mm, preferably between 10 and 20 mm, more preferably around 10 mm.

To meet the transmissivity requirements and UV-stability the inner cylinder 10a or at least the interface wall 11 thereof is preferably made from or at least includes in relevant portions a quartz material that is permeable for radiation in the ultraviolet range, preferably in the range of at least between 150 nm and 200 nm. Quartz glass (fused quartz) is formed from silica in amorphous (non-crystalline) form and differs from traditional glass in that it does not contain other ingredients which are typically added to glass to lower the melting temperature. Quartz glass thus has a high melting point (compared to ordinary glass), a high chemical purity and resistance, a high thermal resistance, a low thermal expansion with high resistance to thermal shocks, and a high radiation resistance. The fused quartz preferably used is a synthetic fused quartz. Furthermore, the (synthetic) fused quartz may comprise a certain content of hydrogenmonoxid (OH) that prevents solarisation in the UV-range and has some absorption peaks in the infrared range.

The radiation source is an excimer lamp 13 (or "excilamp") which is a source of ultraviolet light produced by spontaneous emission of excimer (exciplex) molecules. The main wavelength that is emitted by the excimer lamp 13 in operation depends on the working gas filling of the excimer lamp. Eligible working gases producing radiation in the desired range are Ar, Kr, $I_2$, $F_2$ and $Xe_2$. Excimer lamps are quasi-monochromatic light sources that can operate over a wide range of wavelengths in the ultraviolet (UV) and vacuum ultraviolet (VUV) spectral regions with high power spectral density. The operation of excimer lamps is based on the formation of excited dimers (excimers) and the transition from the bound excited excimer state to a weakly bound ground state resulting in an UV-photon radiation. An excimer lamp radiation wavelength is specified by the working gas also known as an excimer molecule. A particularly preferred excimer lamp for use in the device of the invention is one using Xenon gas ($Xe_2$). The excimer lamp is mercury free, electrodeless and the discharge is based on radiofrequency energy. Thus, this lamp has no ageing effect linked to the number of ON/OFF switching cycles. Compared to a mercury lamp which requires a preheating time of approximately 30 s, the excimer lamp is essentially instantaneously operational, i.e. in less than 10 ms. For example, if the Xenon gas ($Xe_2$) is used as working gas, the emitted radiation has a main wavelength of 172 nm. On the other hand, if Krypton is used as the working gas, the main wavelength would be 146 nm. Moreover, the excimer lamp can be discarded as general electrical waste and does not require special treatment or disposal procedures like mercury lamps.

The main wavelength of the radiation of the excimer lamp 13 preferably used in the invention is preferably below 200 nm, preferably between 150 nm and 200 nm, most preferably 172 nm in case pure xenon gas is used, preferably with a half bandwidth of +/−8 nm relative to the peak intensity, wherein there is still more than 50% of the peak intensity in the range of 164 nm to 180 nm.

Between the interface wall 11 of the inner cylinder 10a and frontal, i.e. vertical surfaces 9b of the baffle plates 9 gaps G are formed through which the fluid must pass on its way through the exposure zone from the inlet to the outlet. These gaps G (as measured in a direction perpendicular to the outer peripheral surface of the interface wall 11, i.e. radial in case of a cylindrical structure, are equal to or smaller than 2.0 mm, preferably in the range from 1.2 mm to 0.3 mm, more preferably in the range from 0.5 mm to 1.0 mm.

Figure 4:
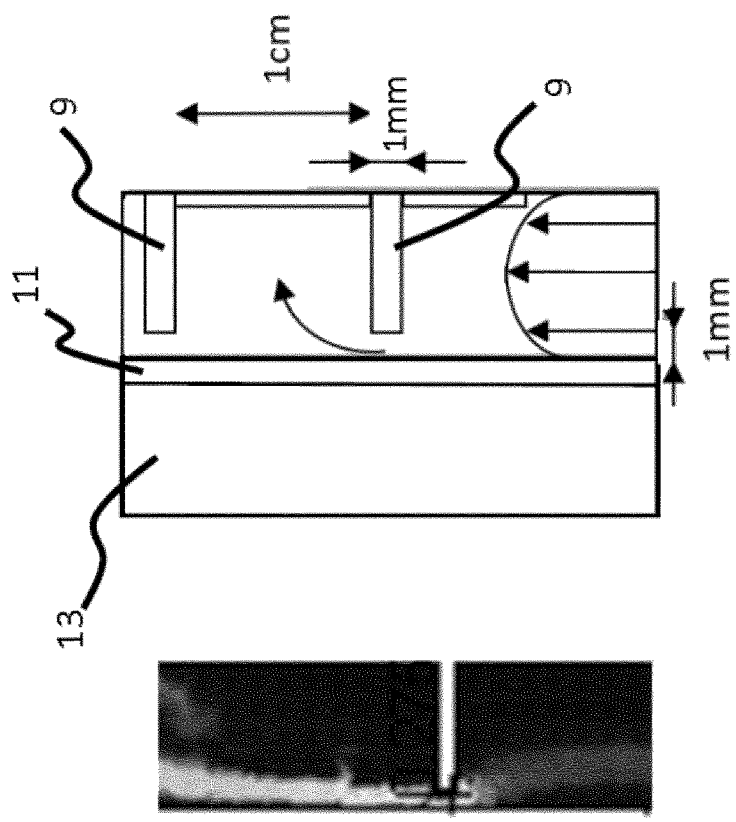
FIG. 4 is a schematic diagram showing the flow situation in the vicinity of the interface wall between the radiation source (lamp) and the flow-through volume of the container with the baffles on the right and a flow simulation on the left.
Figure 3:
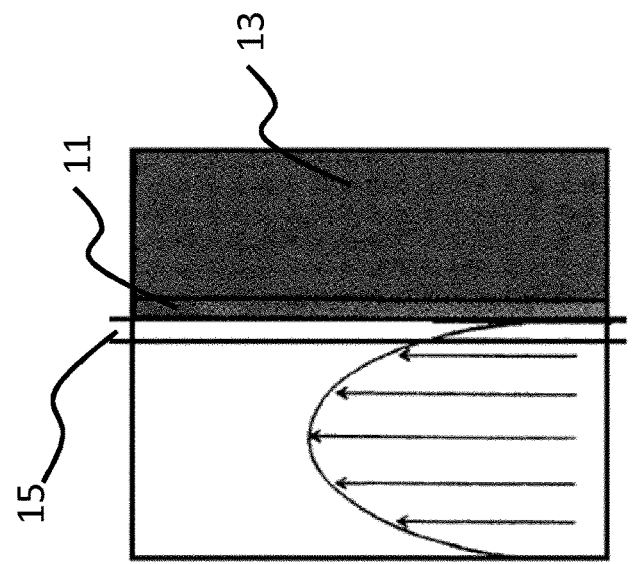
FIG. 3 is a schematic diagram showing the flow situation in the vicinity of the interface wall between the radiation source (lamp) and the flow-through volume of the container without the baffles.
Figure 5:
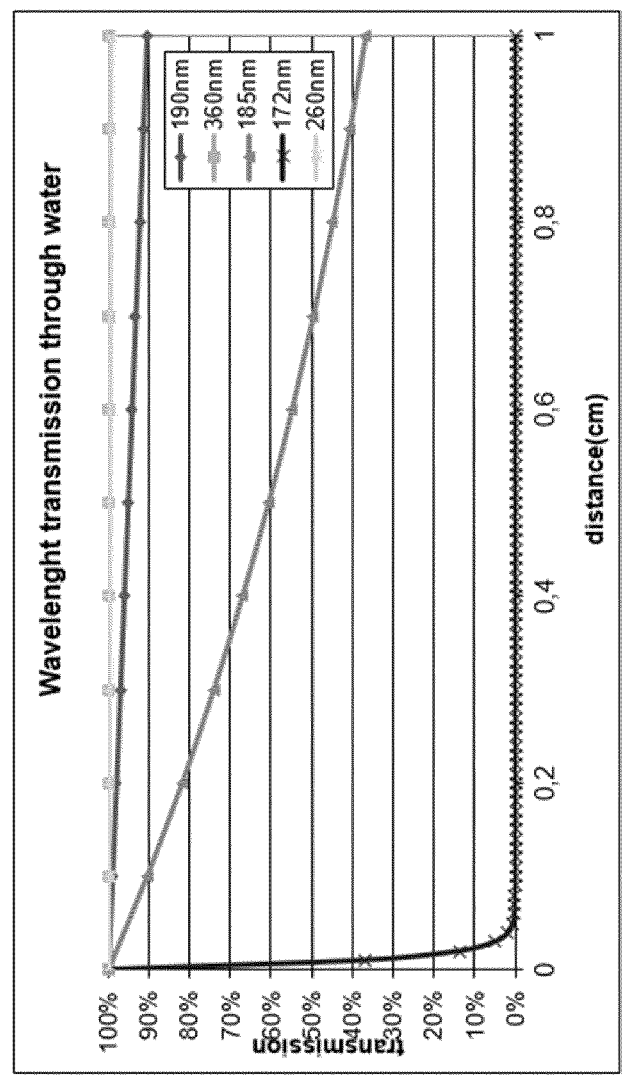
FIG. 5 is a diagram showing an intensity of UV-light as a function of a wavelength of the light and a penetration depth in water.

As shown in FIGS. 2 and 3 the excimer lamp 13 emits radiation, e.g. UV-light, into an area (active oxidation layer) 15 adjacent to the interface wall 11 in the fluid. Due to the (short) wavelength of the excimer lamp 13 the intensity of the emitted light decreases quickly with the increasing penetration depth of the light in the fluid as shown in FIG. 5. Therefore, the size of the gap G between the baffle plates 9 and the interface wall is set to a relatively small value in order to irradiate and penetrate the entire thickness of the fluid layer created by forcing the fluid through the gaps G and along the interface wall 11. Further, since the upper or upstream surfaces 9a of the baffle plates 9 are set to have a right angle with respect to the flow direction along the interface wall 11, small turbulences are generated in the fluid. The smaller the distance, the higher the turbulences. These internal turbulences intermix the fluid in the active oxidation layer 15 near the interface wall by forcing parts of the fluid in alternate intervals toward and away from the interface wall of the inner cylinder 11 and therefore entering and leaving the active oxidation layer 15. Thus, a laminar flow can be prevented and the entire fluid flow passing the baffle plates receives substantially the same level of UV exposure. FIG. 4 shows a conceptual diagram of the expected flow behavior at flow rates of 120 l/h (on the right) and the result of a real-life simulation of the flow at 40 l/h (on the left). For the invention it is important that all fluid entering the device 1 must pass through the gaps G, i.e. avoid bypass flows through the volume 8 at portions where the fluid is not exposed to the radiation.

Figure 6:
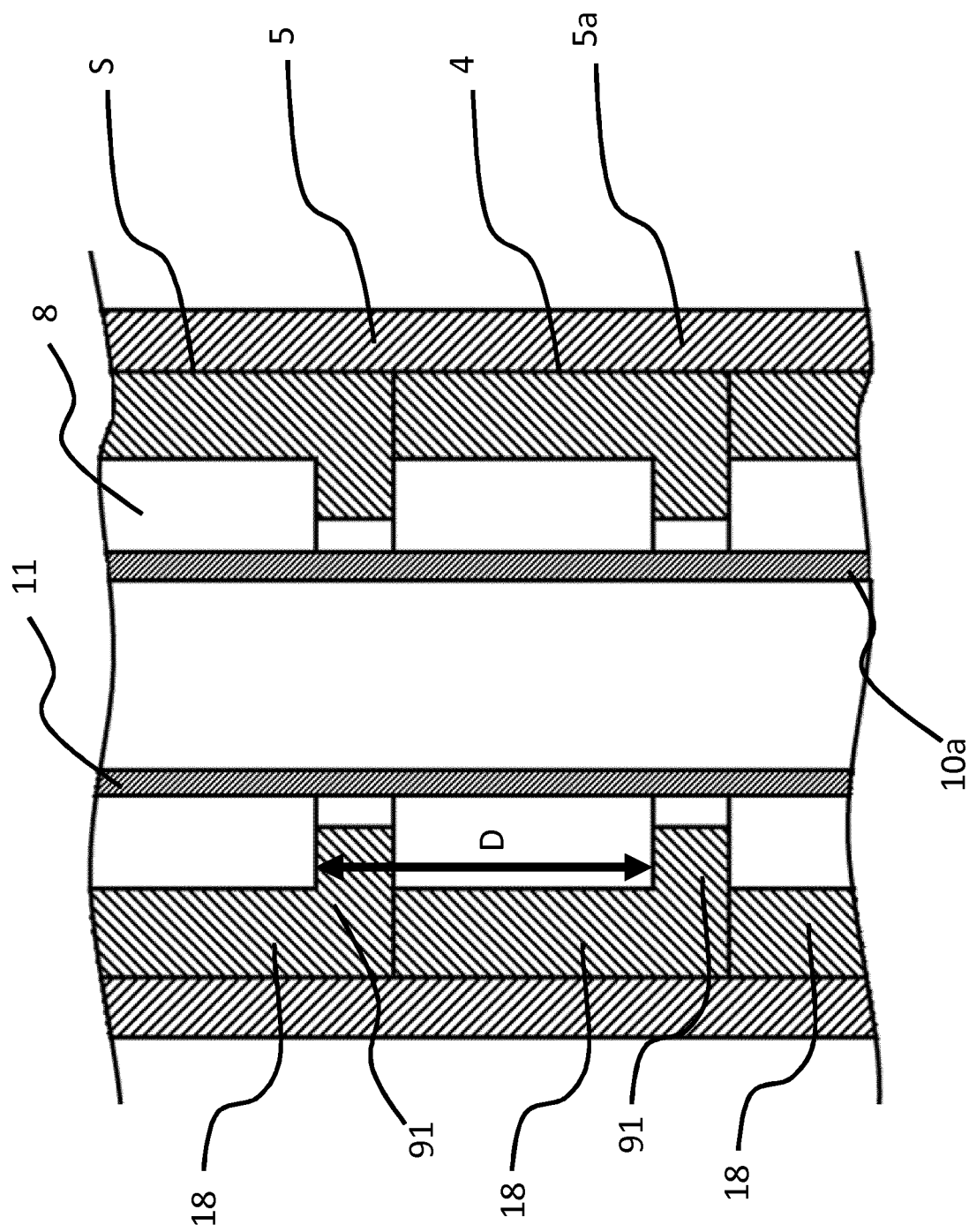
FIG. 6 is an enlarged schematic section view of a purification device with a stack of baffle plates according to an embodiment of the present invention.

Next a further preferred embodiment will be described with reference to FIG. 6. In FIG. 6 elements like the radiation source, inlet and outlet are omitted for convenience of explanation. Different from the above embodiment the baffle plates 91 are not integrally formed with the inner surface of the outer cylinder 5a but the baffle plates 91 are arranged in a stack with a predetermined spacing (inter-baffle distance) D to form a self-supporting element that is mounted into the internal volume 8 of the container 5 (outer cylinder 5a) so as to surround the interface wall 11 of the inner cylinder 10a. In this embodiment the inter-baffle spacing is maintained by spacers 18 which are integrally formed with a respective one of the baffle plates 91.

Figure 7:
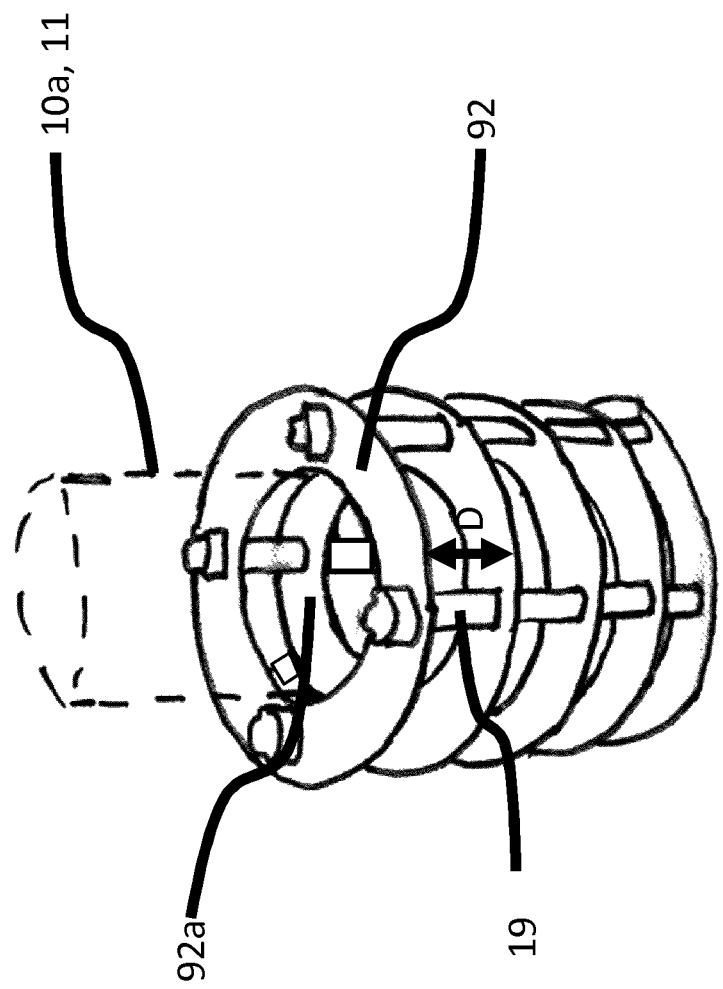
FIG. 7 is a perspective view of a self-supporting baffle stack.

In another embodiment shown in FIG. 7 the self-supporting element is formed by baffles made from a sheet material, i.e. stainless steel or plastics material, in the form of disks 92 with a central hole 92a that are axially interconnected by bolts 19 serving as spacers arranged between the adjacent disks 92 to maintain a constant inter-baffle distance D and distributed around the circumference. The central hole 92a is dimensioned such that it has a sufficiently larger diameter than the outer circumferential wall of the inner cylinder 10a serving as interface wall 11 in order to form the desired gaps G for the flow of the fluid. The outer periphery of the disks 92 can be sealed against the inner circumferential wall 4 of the outer cylinder 5 by the exact dimensioning of the material resulting in a light press fit of the element into the outer cylinder 5, by a certain resiliency (in case of plastics material where the discs are dimensioned slightly larger than the cross section of the outer cylinder) or by separate seals attached to the outer peripheral edges.

For a stable support a minimum of three bolts 19 in a regular distribution would be sufficient but more can be used. This embodiment is not limited to the shown solution and different combinations of spacers 18 and connecting means are possible to achieve the "ladder-like" structure of the self-supporting baffle element. The structure does not necessarily have to be self-supporting in a rigid manner. It should just provide sufficient stability that it can be inserted, as a pre-mounted unit, into the outer cylinder 5a of the container 5 and seal with respect to the inner peripheral surface 4 thereof while maintaining the gap G to the inner cylinder 11 and the inter-baffle distance D. Once inserted the baffles 91, 92 will be maintained in position in the outer cylinder 5. Another modification that provides reduced assembly time and cost would be to punch out baffle discs 92 from a sheet material which have a number of lugs or strips integrally radially protruding from the outer periphery. These lugs or strips can be subsequently bent from the plane of the discs and can then serve as spacers 18 to maintain the inter-baffle distance D. The discs with the lugs can be inserted into the outer cylinder unconnected or the lugs can serve to connect the adjacent discs with each other beforehand to form a unit. The self-supporting modularized construction can reduce the manufacturing and maintenance cost and effort and can provide a large number of variants of the device 1 with a reduced number of different parts.

Figure 8:
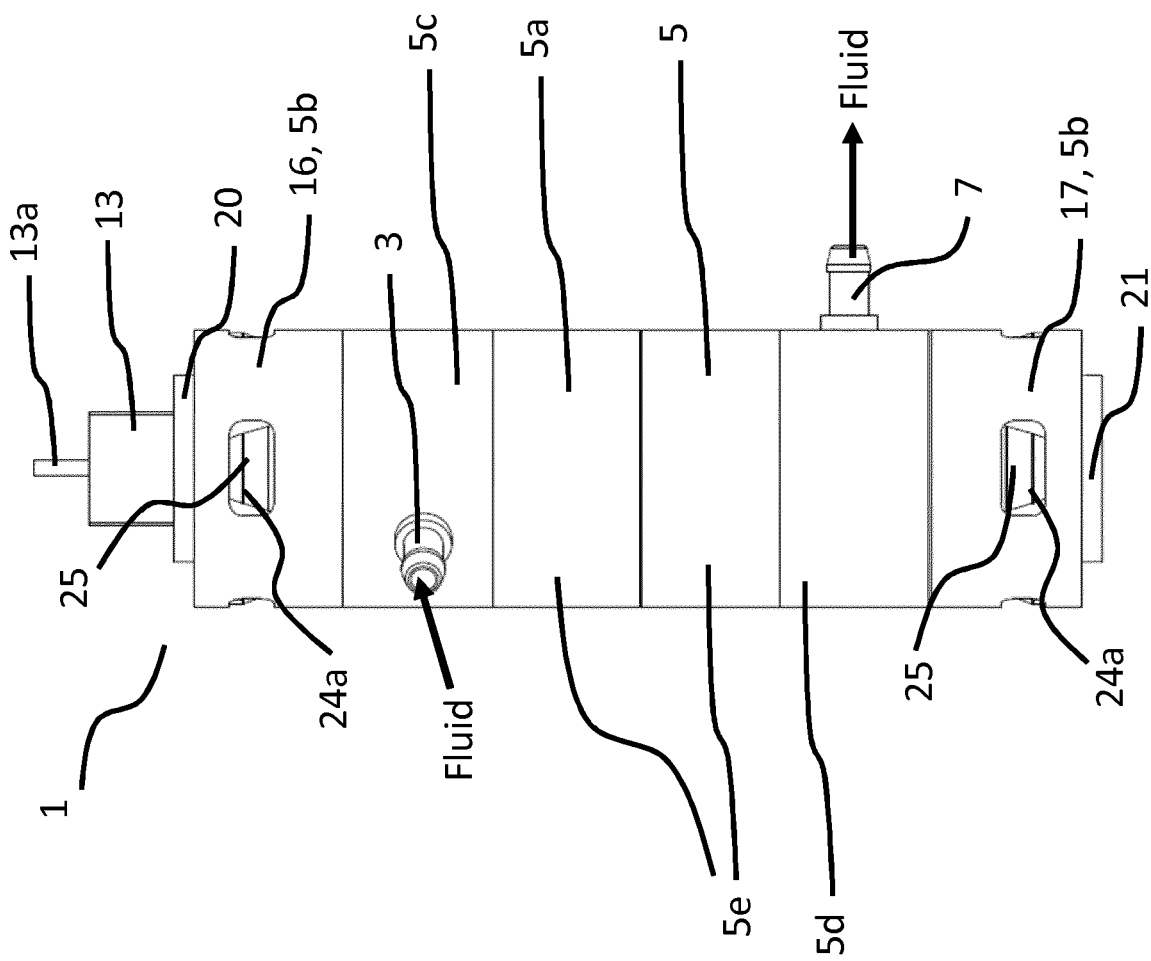
FIG. 8 is a side view of a flow-through purification device according to a preferred embodiment.
Figure 9:
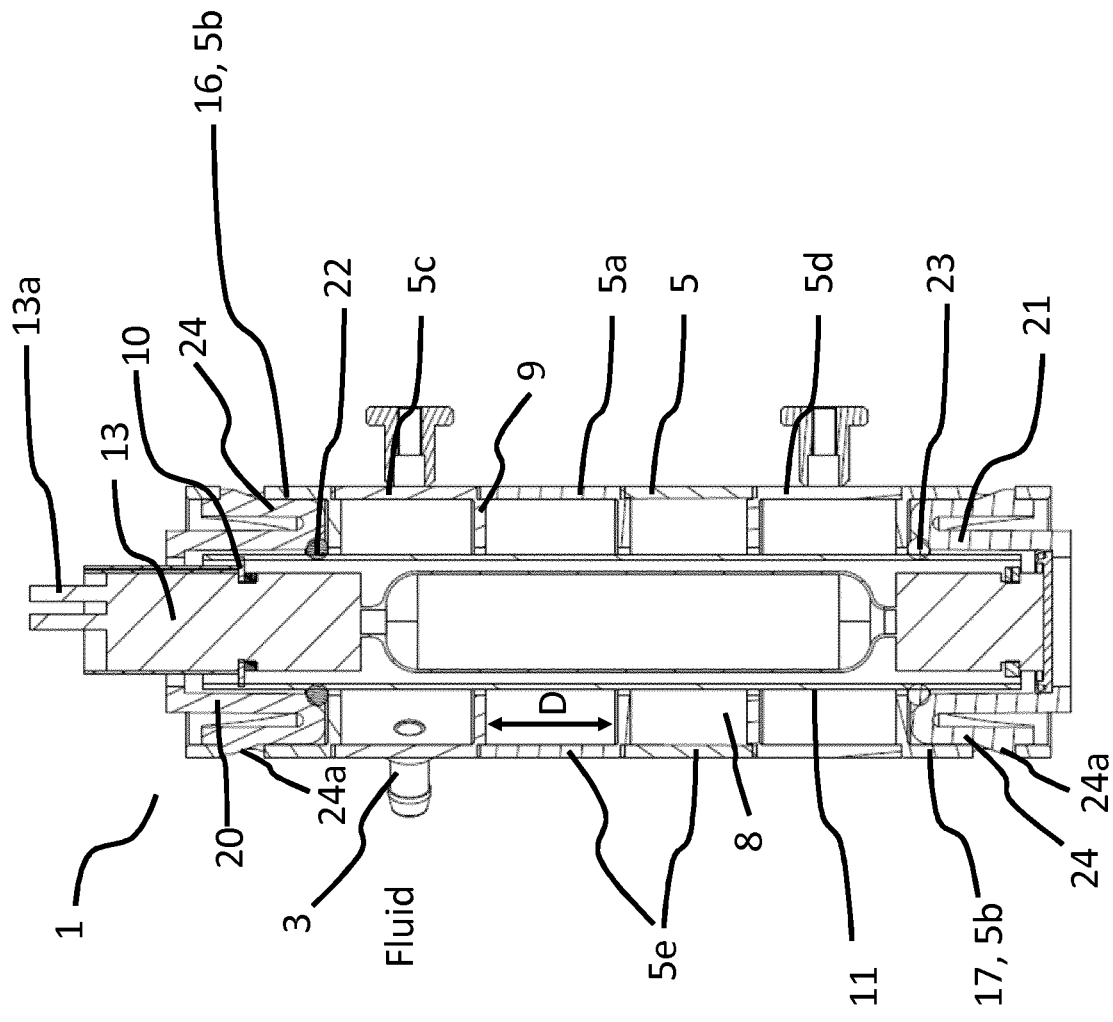
FIG. 9 is a cross-section view of the flow-through purification device of FIG. 8.
Figure 10:
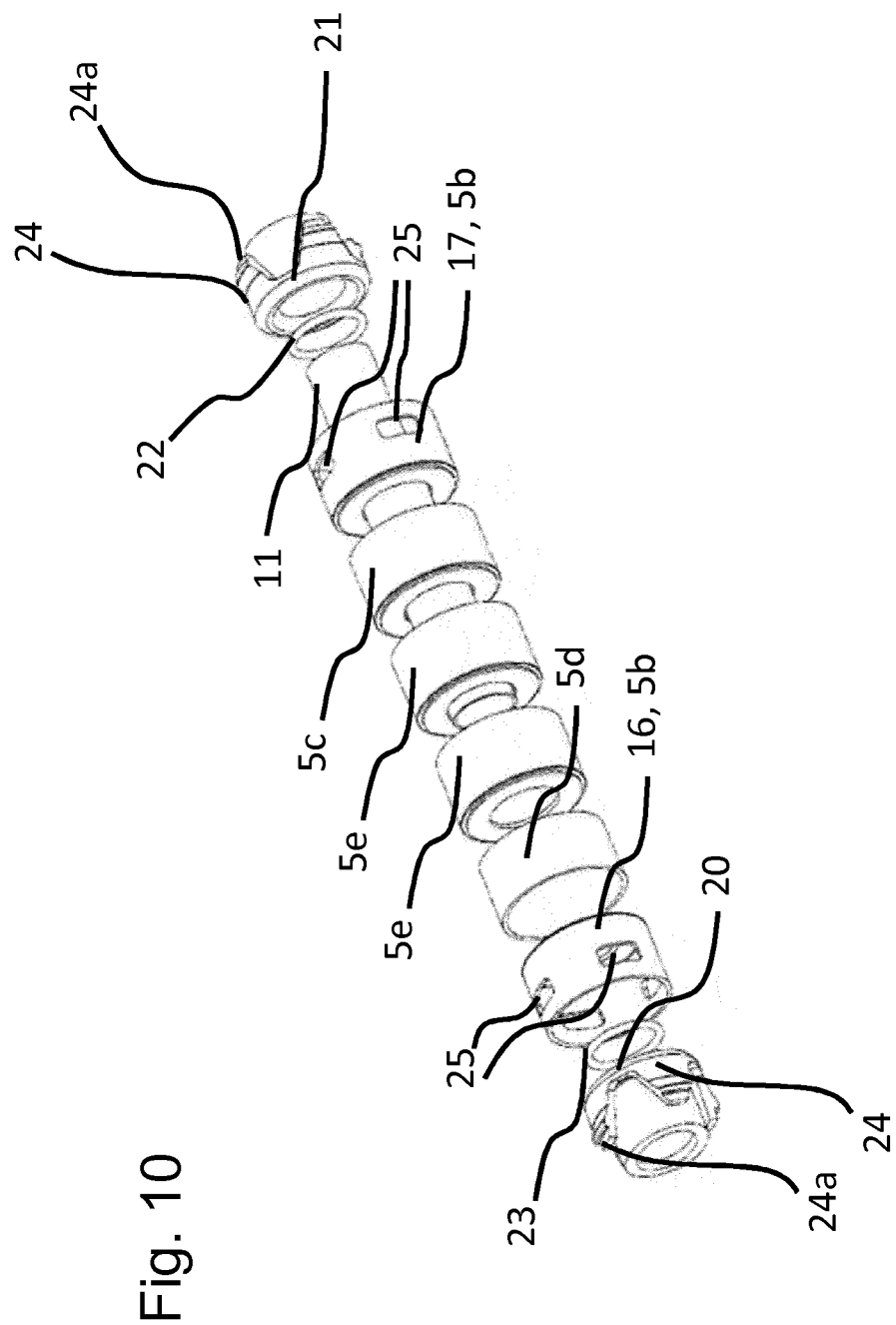
FIG. 10 is a perspective explosion illustration of the flow-through purification device of FIG. 8.

The FIGS. 8, 9 and 10 show an actual example of the device of the invention in a side view from the outside, in a partial cross sectional view and in an explosion illustration without showing the excimer lamp. The various elements of the device are identified with the same reference signs as in the previously described schematic embodiments.

The container 5 is formed with a plurality of axially arranged cylinder parts 5b, 5c, 5d and 5e connected to each other by welding to form the fluid-tight outer cylinder 5a (outer cylinder assembly). Preferably the cylinder parts are connected to each other by Tungsten Inert Gas (TIG) welding. TIG welding is an arc welding process that uses a non-consumable tungsten electrode to produce the weld and that can be performed together with or without a filler metal, whereby the latter case is known as autogenous welding and is the most preferable welding method for the embodiment. The weld zone is protected from atmospheric contamination by an inert shielding gas which leads to strong and clean connections, and the TIG welding provides a high level of process control and is thus especially suitable for thin materials to be welded. Here, orbital welding is the most preferred welding method for the TIG welding due to the cylindrical shape of the cylinder parts that are to be connected. In orbital welding the arc is mechanically rotated through 360° around a static work piece.

The cylinder parts 5e forming the exposure zone of the outer cylinder 5a have the baffle plates 9 integrally formed and protruding radially inward from an outer cylindrical peripheral wall.

The inlet 3 and outlet 7 (not visible in the rotated position in FIG. 9) are formed on separate cylinder parts 5c, 5d placed adjacent to the axial end portions of the outer cylinder 5a defining the oxidation zone and are attached to the cylinder parts forming the exposure zone by separate connectors or are integrally connected by welding (as shown in FIGS. 8 and 9).

Two end caps 20, 21, each one arranged to close one of the two axial ends of the outer cylinder 5a, are releasably engaged with locking cylinder parts 16 (or 5b), 17 (or 5b) of the outer cylinder 5a through a snap-connection (described later). The end caps thus fluid tightly close the inner volume of the cylinder 5 where the fluid flows at the axial ends thereof to the environment.

The cylinder parts 5b, 5c and 5e connected to each other by welding to form the fluid-tight outer cylinder 5a (outer cylinder assembly) can—except the cylinder part 5d—all have the same basic "cup- or pot-like" design and essentially identical outer dimensions. For this basic design the cylinder parts 5b, 5c and 5e are respectively formed from metal, preferably stainless steel, by deforming (deep drawing) a stamped sheet material into the "cup- or pot-like" form where the bottom forms the baffle plate 9 and the peripheral circumferential wall forms the outer wall of the outer cylinder 5a. Beside the advantage of UV stability metal also provides the capability of dissipating heat generated by the operation of the radiation source to the environment, i.e. air. Thus an increase in water temperature can be suppressed.

The locking cylinder parts 16, 17 (5b) are cylinder parts with the "cup- or pot-like" design similar to the cylinder parts 5e forming the exposure zone and the cylinder part 5c provided with the inlet with the difference of having four holes 25 serving as locking openings in the peripheral wall. The locking cylinder parts 16, 17 (5b) in the embodiment are identical but are connected in the outer cylinder 5a in opposite orientation so that their bottom is in both cases located to the inside.

This necessitates the use of a single different cylinder part 5d that can be identical to the other "cup- or pot-shaped" cylinder parts with respect to the peripheral circumferential wall but has no bottom. In this case the outlet 7 is provided on this ring-shaped cylinder part 5d. Of course, it is also possible to use the ring-shaped cylinder part (without the bottom) instead of one of the cylinder parts 5e forming the exposure zone and to orient the adjacent cylinder part, be it a cylinder part 5e or a cylinder part 5c with an inlet/outlet, with the bottom in an inverted orientation in the stack of cylinder parts forming the outer cylinder 5a.

The end caps 20, 21 have a plug-like design and include a cylindrical annular main body and four elastic legs 24 serving as connection portions in that they are provided with hook-like protrusions 24a protruding radially outward from free ends of the legs 24 arranged to engage with the holes 25 of the locking cylinder parts 16, 17 in order to releasably attach the end caps to the locking cylinder parts 16, 17. The legs 24 are equidistantly distributed about an outer periphery of the cylindrical annular main body, protrude upward therefrom and are inclined radially outward. The cylindrical main body of the end cap 20, 21 has a slightly smaller outer diameter than an inner diameter of locking cylinder part 16, 17 and the inner diameter of the main body is slightly larger than the outer diameter of the inner cylinder 10a. The legs are integrally connected to the main body of the end cap 20, 21, so that the outer diameter of the end cap 20, 21 as a whole becomes larger than an inner diameter of the locking cylinder part 16, 17. By inserting the end cap 20, 21 into the locking cylinder part 16, 17 the legs are pressed radially inward against their resiliency and, when the end cap 20, 21 is fully inserted into the respective locking cylinder part 16, 17 and the hook-like protrusions 24a are aligned with the respective holes, the protrusions snap, i.e. click into place in the respective holes of the end cap 20, 21 and are form-locking held in the holes.

The pressure inside the container, i.e. the occurring reaction forces due to this pressure are acting on the connection portions. Therefore, the dimensions of the projections, their form and the strength and elasticity of the legs and their number have to be selected to withstand these forces and to avoid that the legs break or that the projections slip out of the holes in operation. The pressure inside the container in operation can be up to 24 bar which is equivalent to 3000 N acting on the connection portions. The invention is not limited to four legs of course. The end caps can be formed as an integral component from plastics material, preferably those that have UV stability as the materials described above in connection with the baffle plates.

Before the end caps 20, 21 are inserted the inner cylinder 10a serving as receptacle for the radiation source (excimer lamp) 13 is inserted into the outer cylinder 5. The excimer lamp 13 can be inserted into the inner cylinder before or after the same is inserted into the outer cylinder. The excimer lamp can be fixed in the inner cylinder by suitable connectors, be it releasable or fixed. As shown in FIGS. 8 and 9 the excimer lamp 13 has electrical connectors 13a protruding from one of the axial end portions of the device 1 so that current for operating the same can be applied.

Before the end caps are inserted an O-ring 22, 23 is respectively fit on the inner cylinder 10a and put in place until it covers the gap provided between the central hole in the bottom of the locking cylinder parts 5b and the inner cylinder 10a (see FIGS. 9 and 10). When the end caps are fully inserted and engaged with the locking cylinder parts, the O-ring is compressed in place to provide fluid tightness of the inner volume of the container 5 where the fluid to be processed flows. At the same time the compressed O-ring also holds and fixes the inner cylinder 10a (receiving the excimer lamp 13) in place in the outer cylinder 5.

Thus, the insertion opening of the inner cylinder for inserting/removing the excimer lamp 13 is accessible to the outside of the device even after closing the inner volume of the container between the inner and outer cylinders by attaching the end caps to facilitate maintenance and manufacturing. In other words, the entire device can be prefabricated without the excimer lamp 13 which can be subsequently mounted to the device or the excimer lamp can be changed and/or temporarily removed for cleaning or repairing the other parts of the device. Also, different radiation sources can be used with the same device provided they fit into the receptacle formed by the inner cylinder.

The structure of the outer cylinder 5a being formed from stacked, i.e. axially aligned and welded cylinder parts of substantially identical basic design provides advantages with respect to manufacturing simplicity and cost. Further, a range of devices with different axial length, capacity and throughput can be easily set up with a small number of different components in a modular construction. Devices having a longer axial length of the oxidation zone can provide a lower TOC of the purified water at the outlet.

As described above the outer cylinder 5a is closed by providing two end caps 20, 21 on both axial ends thereof. Nevertheless, it is also possible to provide only one end cap 20, 21 at one axial end of the outer cylinder 5a and to close the other end by providing a further cylinder part (not shown) having a completely closed bottom and connected by welding to the penultimate cylinder part in the stack of cylinder parts forming the outer cylinder 5a. Furthermore, the end cap(s) 20, 21 can also be connected to the outer cylinder 5a by other releasable connection means like a bajonet- or thread-type connection that provide for an application of the required axial force to compress the O-ring or can be fixedly attached in a manner that cannot be removed without destruction, i.e. by welding or glueing.

REFERENCES 1 device
3 inlet
4 inner peripheral wall
5 outer container
5a outer cylinder
5b, 5c, 5d, 5e cylinder part
7 outlet
8 volume
9, 91 baffle plate
10 receptacle
10a inner cylinder
11 interface wall
13 radiation source (excimer lamp)
15 active oxidation layer
16, 17 locking cylinder part
18 spacers
19 bolts
20, 21 end cap
22, 23 O-ring
24 leg
24a projection
25 hole
D inter-baffle distance
G gap
T thickness

The invention claimed is:

1. A flow-through fluid purification device comprising:
a container arranged such that fluid to be purified can flow-through a volume of the container from an inlet to an outlet;
a receptacle for accommodating a radiation source in the form of a lamp, wherein the receptacle has an interface wall permeable for radiation with a wavelength in the UV-range, and arranged to let radiation pass into the volume of the container;
a plurality of baffle plates located in the volume of the container with an inter-baffle distance (D) in the flow direction from the inlet to the outlet,
wherein the baffle plates are arranged to force the fluid flowing from the inlet to the outlet to flow substantially along the interface wall and through gaps (G) between the interface wall and the baffle plates defining the shortest distance between the interface wall and the baffle plates,
wherein the baffle plates each have a surface on the upstream side in the flow direction which is perpendicular to the interface wall, and
wherein the lamp is an excimer lamp configured to emit radiation with a wavelength between 150 nm and 200 nm.

2. The device according to claim 1, wherein the gaps (G) are equal to or smaller than 2.0 mm.

3. The device according to claim 1, wherein the baffle plates have a thickness (T) parallel to the interface wall, at least in a portion adjacent to the gap (G), of less than 1.5 mm.

4. The device according to claim 1, wherein the inter-baffle distance (D) between the upstream surfaces of two consecutive baffle plates, at least adjacent to the gap (G), is in the range from 4 to 30 mm.

5. The device according to claim 1, wherein the number of baffle plates in the flow direction along the interface wall is at least 4.

6. The device according to claim 1, wherein the baffle plates are interconnected with each other.

7. The device according to claim 6, wherein the baffle plates form a self-supporting element.

8. The device according to claim 6, wherein a seal (S) is provided between an inner peripheral wall of the container and the outer peripheral side of the baffle plates and/or an outer peripheral side of spacers.

9. The device according to claim 1, wherein the baffle plates are integrally formed with a wall of the container.

10. The device according to claim 1, wherein the baffle plates are formed from metal.

11. The device according to claim 1, wherein the baffle plates are formed from plastics materials that have UV stability.

12. The device according to claim 1, wherein the container has an outer cylinder and the interface wall of the receptacle is formed by an outer peripheral wall of an inner cylinder inserted into the volume of the outer cylinder with the baffle plates located between the outer cylinder and the inner cylinder; and the device has at least one end cap engaged with an axial end of the outer cylinder, arranged to hold the inner cylinder in position in the outer cylinder and to fluid-tightly close the outer cylinder.

13. The device according to claim 1, wherein the interface wall comprises or is formed from quartz glass.

14. The device according to claim 1, wherein the radiation source is located so as to be separated from the fluid in the volume of the container by the interface wall.

15. The device according to claim 11, wherein the plastics materials having UV stability is selected from the group consisting of polytetrafluorethylene, PVDF, PEEK, PFA, polyetherimide and PE.

16. The device according to claim 11, wherein the plastic material is provided with a metallic coating.

17. The device according to claim 14, wherein the excimer lamp is configured to emit radiation with a wavelength of 172±8 nm.

\* \* \* \* \*